United States Patent
Ki et al.

(10) Patent No.: US 12,163,194 B2
(45) Date of Patent: Dec. 10, 2024

(54) ARTIFICIAL-INTELLIGENCE-BASED CANCER DIAGNOSIS AND CANCER TYPE PREDICTION METHOD

(71) Applicants: GC GENOME CORPORATION, Gyeonggi-do (KR); AIMA CO., LTD., Seoul (KR)

(72) Inventors: Chang-Seok Ki, Gyeonggi-do (KR); Eun Hae Cho, Gyeonggi-do (KR); Junnam Lee, Gyeonggi-do (KR); Jin Mo Ahn, Gyeonggi-do (KR); Joohyuk Sohn, Seoul (KR); Gun Min Kim, Seoul (KR); Min Hwan Kim, Gyeonggi-do (KR)

(73) Assignees: GC GENOME CORPORATION, Gyeonggi-Do (KR); AIMA CO., LTD., Seoul (KR)

( * ) Notice: Subject to any disclaimer, the term of this patent is extended or adjusted under 35 U.S.C. 154(b) by 0 days.

(21) Appl. No.: 18/003,455

(22) PCT Filed: Nov. 15, 2021

(86) PCT No.: PCT/KR2021/016612
§ 371 (c)(1),
(2) Date: Dec. 27, 2022

(87) PCT Pub. No.: WO2022/114631
PCT Pub. Date: Jun. 2, 2022

(65) Prior Publication Data
US 2023/0183812 A1    Jun. 15, 2023

(30) Foreign Application Priority Data
Nov. 27, 2020  (KR) ........................ 10-2020-0162183

(51) Int. Cl.
*C12Q 1/6886*  (2018.01)
*G16B 40/20*  (2019.01)

(52) U.S. Cl.
CPC ........... *C12Q 1/6886* (2013.01); *G16B 40/20* (2019.02); *C12Q 2600/118* (2013.01)

(58) Field of Classification Search
None
See application file for complete search history.

(56) References Cited

U.S. PATENT DOCUMENTS

| | | | |
|---|---|---|---|
| 7,244,567 | B2 | 7/2007 | Chen et al. |
| 10,360,499 | B2 | 7/2019 | Kumar et al. |
| 2006/0246497 | A1 | 11/2006 | Huang et al. |
| 2006/0275779 | A1 | 12/2006 | Li et al. |
| 2007/0087362 | A1 | 4/2007 | Church et al. |
| 2007/0122347 | A1 | 5/2007 | Statnikov et al. |
| 2007/0194225 | A1 | 8/2007 | Zorn |
| 2019/0065676 | A1 | 2/2019 | Duenwald et al. |
| 2019/0189242 | A1 | 6/2019 | Angiuoli et al. |
| 2019/0316209 | A1 | 10/2019 | Hubbell et al. |

FOREIGN PATENT DOCUMENTS

| | | |
|---|---|---|
| KR | 101950395 B1 | 2/2019 |
| KR | 1020190036494 A | 4/2019 |
| KR | 101984611 B1 | 5/2019 |
| KR | 1020190048926 A | 5/2019 |
| KR | 1020200004204 A | 1/2020 |
| KR | 1020200108938 A | 9/2020 |
| WO | 2016094330 A2 | 6/2016 |
| WO | 2019055835 A1 | 3/2019 |
| WO | 2019232435 A1 | 12/2019 |
| WO | 2020232109 A1 | 11/2020 |

OTHER PUBLICATIONS

"Applied Biosystems, Carlsbad, California, USA", Applied Biosystems, 2009.
Bellman, R., Chapter 1, Dynamic Programming, 2003, Publisher: Princeton University Press.
Branton, D., et al., "The potential and challenges of nanopore sequencing", Nature Biotechnology, 2008, pp. 1146-1153, vol. 26, No. 10, Publisher: Nature Publishing Group.
Butler, J., et al., Allpaths De novo assembly of whole-genome shotgun microbeads, Genome Research, 2008, pp. 810-820, vol. 18, Publisher: Cold Spring Harbor Laboratory Press.
Campagna, D., et al., "Pass a program to align short sequences", Bioinformatics, 2009, pp. 967-968; doi:10.1093/bioinformatics/btp087, vol. 25, No. 7, Publisher: Oxford University Press.
Chen Y., et al., "PerM efficient mapping of short sequencing reads with periodic full sensitive spaced seeds", Bioinformatics, 2009, pp. 2514-2521; doi:10.1093/bioinformatics/btp486, vol. 25, No. 19.
Clement, N.L., et al., "The GNUMAP algorithm unbiased probabilistic mapping of oligonucleotides from next-generation sequencing", Bioinformatics, 2010, pp. 38-45, vol. 26, No. 1, Publisher: Oxford University Press.
De Bona, F., et al., "Optimal spliced alignments of short sequence reads", Bioinformatics, 2008, pp. i174-i180, vol. 24, No. 16, Publisher: Oxford University Press.

(Continued)

*Primary Examiner* — G. Steven Vanni
(74) *Attorney, Agent, or Firm* — HULTQUIST, PLLC; Steven J. Hultquist

(57) ABSTRACT

The present invention relates to an artificial-intelligence-based cancer diagnosis and cancer type prediction method, and, more particularly, to an artificial-intelligence-based cancer diagnosis and cancer type prediction method, which extracts nucleic acids from a biological sample to acquire sequence information, and thus generate vectorized data on the basis of aligned nucleic acid fragments, and then inputs same into a trained artificial intelligence model to analyze a calculated value. Compared with a conventional method, which uses a step of determining the number of chromosomes on the basis of a read count and utilizes each related value as a normalized value, the artificial-intelligence-based cancer diagnosis and cancer type prediction method according to the present invention generates vectorized data to perform an analysis using an AI algorithm, and thus is useful in that similar effects can be exhibited even when read coverage is low.

12 Claims, 4 Drawing Sheets

(56) References Cited

OTHER PUBLICATIONS

Eaves, H.L., et al., "MOM maximum oligonucleotide mapping", Bioinformatics, 2009, pp. 969-970; doi.10.1093/bioinformatics/btp092, vol. 25, No. 7, Publisher: Oxford University Press.

Edwards, J.R., et al., "Mass-spectrometry DNA sequencing", Mutation Research, 2005, pp. 3-12, vol. 573, Publisher: Elsevier.

Fahlgren, N., "Computational and analytical framework for small RNA profiling by high-throughput sequencing", RNA, 2009, pp. 992-1002, vol. 15, Publisher: ResearchGate.

Gnirke, A., et al., "Solution hybrid selection with ultra-long oligonucleotides for massively parallel targeted sequencing", Nature Biotechnology, 2009, pp. 182-189, vol. 27, No. 2, Publisher: Nature America, Inc.

Hanna, G.J., et al., "Comparison of Sequencing by Hybridization and Cycle Sequencing for Genotyping of Human Immunodeficiency Virus Type 1 Reverse Transcriptase", Journal of Clinical Microbiology, 2000, pp. 2715-2721, vol. 38, No. 7, Publisher: American Society for Microbiology.

Hinton, G., et al., "Deep Neural Networks for Acoustic Modeling in Speech Recognition", IEEE Signal Processing Magazine, 2012, pp. 82-97, vol. 29, No. 6.

Homer, N., et al., "BFAST An Alignment Tool for Large Scale Genome Resequencing", PLoS ONE, 2009, e7767, vol. 4, No. 11, Publisher: www.plosone.org.

Jiang, H., et al., "SeqMap mapping massive amount of oligonucleotides to the genome", Bioinformatics, 2008, pp. 2395-2396; doi:10.1093/bioinformatics/btn429, vol. 24, No. 20, Publisher: Oxford University Press.

Kent, W.J., "BLAT—The Blast-Like Alignment Tool", Genome Research, 2002, vol. 12, No. 656-664, Publisher: Cold Spring Laboratory Press.

Kim, Y.J., et al., "ProbeMatch rapid alignment of oligonucleotides to genome allowing both gaps and mismatches", Bioinformatics, 2009, pp. 1424-1425; doi:10.1093/bioinformatics/btp178, vol. 25, No. 11, Publisher: Oxford University Press.

Krishnakumar, S., et al., "A comprehensive assay for targeted multiplex amplification of human DNA sequences", PNAS, 2008, pp. 9296-9310; www.pnas.org/cgi/doi/10.1073/pnas.0803240105, vol. 105, No. 27.

Langmead, B., et al., "Ultrafast and memory-efficient alignment of short DNA sequenes to the human genome", Genome Biology, 2009, doi:10.1186/GB-2009-10-3-r25, vol. 10, No. R25.

Lasken, R.S., "Single-cell genomic sequening using Multiple Displacement Amplification", Current Opinion in Microbiology, 2007, pp. 510-516, vol. 10, Publisher: Elsevier.

Li, H., et al., "Mapping short DNA sequencing reads and calling variants using mapping quality scores", Genome Research, 2008, pp. 1851-1858, vol. 18, Publisher: CSH Press.

Li, R., et al., "SOAP: short oligonucleotide alignment program", Bioinformatics, 2008, pp. 713-714; doi:10.1093/bioinformatics/btn025, vol. 24, No. 5, Publisher: Oxford University Press.

Li, H., et al., "Fast and accurate short read alignment with Burrows-Wheeler transform", Bioinformatics, 2009, pp. 1754-1760; doi:10.1093/bioinformatics/btp324, vol. 25, No. 14.

Li, R., et al., "SOAP2 an improved ultrafast tool for short read alignment", Bioinformatics, 2009, pp. 1966-1967; doi:10.1093/bioinformatics/btp336, vol. 25, No. 15, Publisher: Oxford University Press.

Li, H., et al., "Fast and accurate long-read alignment with Burrows-Wheeler transform", Bioinformatics, 2010, pp. 589-595; doi:10.1093/bioinformatics/btp698, vol. 26, No. 5.

Lunter, G, et al., "Stampy: A statistical algorithm for sensitive and fast mapping of Illumina sequence reads", Genome Research, 2011, pp. 936-939, vol. 21, Publisher: Cold Spring Harbor Laboratory Press.

Malhis, N., et al., "Slider-maximum use of probability information for alignment of short sequence reads and SNP detection", Bioinformatics, 2009, pp. 6-13; doi:10.1093/bioinformatics/btn565, vol. 25, No. 1.

Metzker, M.L., "Sequencing technlogies-the next generation", Nature Reviews/Genetics, 2010, pp. 31-46, vol. 11, Publisher: Macmillan Publishers Limited.

Muller, T., et al., "Non-symmetric score matrices and the detection of homologous transmembrane proteins", Bioinformatics, 2001, pp. S182-S189, vol. 17, No. 1, Publisher: Oxford University Press.

Ning, Z., et al., "SSAHA: A Fast Search Method for Large DNA Databases", Genome Research, 2001, pp. 1725-1729, vol. 11, Publisher: Cold Harbor Laboratory Press.

Ondov, B.D., et al., "Efficient mapping of Applied Biosystems SOLiD sequence data to a reference genome for functional genomic applications", Bioinformatics, 2008, pp. 2776-2777; doi:10.1093/bioinformatics/btn512, vol. 24, No. 23.

Porreca, G.J., et al., "Multiplex amplification of large sets of human exons", Nature Methods, 2007, pp. 931-936, vol. 4, No. 11, Publisher: Nature Publishing Group.

Prufer, K., et al., "PatMaN rapid alignment of short sequences to large databases", Bioinformatics, 2008, pp. 1530-1532; doi:10.1093/bioinformatics/btn223, vol. 24, No. 13.

Rumble, S.M., et al., "SHRiMP Accurate Mapping of Short Colorspade Reads", PLoS Computational Biology, 2009, e1000386, vol. 5, No. 5.

Salmela, L., "Correction of sequencing errors in a mixed set of reads", Bioinformatics, 2010, pp. 1284-1290; doi:10.1093/bioinformatics/btq151, vol. 26, No. 10, Publisher: Oxford University Press.

Schatz, M. C., "CloudBurst: highly sensitive read mapping with MapReduce", Bioinformatics, 2009, pp. 1363-1369; doi.10.1093/bioinformatics/btp236, vol. 25, No. 11.

Shi, H, et al., "A Parallel Algorithim for Error Correction in High-Throughput Short-Read Data on CUDA-Enabled Graphics Hardware", Journal of Computational Biology, 2010, pp. 603-615; DOI:10.1089/cmb.2009.0062, vol. 17, No. 4, Publisher: Mary Ann Liebert, Inc.

Smith, A.D., et al., "Updates to the RMAP short-read mapping software", Bioinformatics, 2009, pp. 2841-2842; doi:10.1093/bioinformatics/btp533, vol. 25, No. 21, Publisher: Oxford University Press.

Sun, Y., et al., "Identification of 12 cancer types through genome deep learning", Scientific Reports, 2019, https://doi.org/10.1038/s41598-019-53989-3, vol. 9, No. 17256, Publisher: www.nature.com/scientificreports.

Tewhey, R., et al., "Microdroplet-based PCR enrichment for large-scale targeted sequencing", Nature Biotechnology, 2009, pp. 1025-1031, vol. 27, No. 11, Publisher: Nature Publishing Group.

Trapnell, C., "How to map billions of short reads onto genomes", Nature Biotechnology, 2009, pp. 455-457, vol. 27.

Turner, E.H., et al., "Massively parallel exon capture and library-free resequencing across 16 genomes", Nature Methods, 2009, pp. 315-316, vol. 6, No. 5, Publisher: Nature America, Inc.

Warren, R.L., et al., "Assembling millions of short DNA sequences using SSAKE", Bioinformatics, 2007, pp. 500-501; doi:10.1093/bioinformatics/btl629, vol. 23, No. 4.

Weese, D., et al., "RazerS-fast read mapping with sensitivity control", Genome Research, 2009, pp. 1646-1654, vol. 19, Publisher: Cold Spring Harbor Laboratory Press.

Wu, T.D., et al., "GMAP a genmic mapping and alignment program for mRNA and EST sequences", Bioinfomatics, 2005, pp. 1859-1875, vol. 21, No. 9.

Wu, T.D., et al., "Fast and SNP-tolerant detection of complex variants and splicing in short reads", Bioinformatics, 2010, pp. 873-881, vol. 26, No. 7, Publisher: Oxford University Press.

Yuan, Y., et al., "Cancer type prediction based on coy number aberration and chromatin 3D sructure with convolutional neutral networks", BMC Genomics, 2018, https://doi.org/10.1186/s12864-018-4919-z, vol. 19, No. 6 (565), Publisher: CrossMark.

Zerbino, D.R., et al., "Velvet: Algorithms for de novo read assembly using de Bruijn graphs", Genome Research, 2008, pp. 821-829, vol. 18, Publisher: Cold Spring Harbor Laboratory Press.

Office Action issued on Jul. 23, 2024 for Japanese Patent Application 2023-532698.

English Translation of Office Action issued on Jul. 23, 2024 for Japanese Patent Application 2023-532698.

(56) References Cited

OTHER PUBLICATIONS

Office Action issued on Jul. 11, 2024 for Australian Patent Application 2021387426.
Greer, B.T., et al., "Diagnostic Classification of Cancer Using DNA Microarrays and Artificial Intelligence", Ann. N. Y. Acad. Sci., 2004, pp. 49-66, vol. 1020, Publisher: New York Academy of Sciences.
Angermueller, C., et al., "Deep learning for computational biology", Molecular Systems Biology, 2016, DOI: 10.15252/msb.20156651, vol. 12, No. 878.
Cristiano, S., et al., "Genome-wide cell-free DNA fragmentation in patients with cancer", Nature, 2019, pp. 385-389, vol. 570, No. 7761, Publisher: www.nature.com/nature.
Search report issued on Aug. 27, 2024 for European patent application No. 21898457.3.
Office Action issued on Sep. 23, 2024 for Korean patent application No. 10-2020-0162183.
English Translation of Office Action issued on Sep. 23, 2024 for Korean patent application No. 10-2020-0162183.

ARTIFICIAL-INTELLIGENCE-BASED CANCER DIAGNOSIS AND CANCER TYPE PREDICTION METHOD

CROSS-REFERENCE TO RELATED APPLICATIONS

This application is a U.S. national phase under 35 U.S.C. § 371 of International Patent Application No. PCT/KR2021/016612 filed Nov. 15, 2021, which in turn claims priority under 35 U.S.C. § 119 of Korean Patent Application No. 10-2020-0162183 filed Nov. 27, 2020. The disclosures of all such applications are hereby incorporated herein by reference in their respective entireties, for all purposes.

TECHNICAL FIELD

The present invention relates to a method for diagnosing cancer and predicting the type of cancer based on artificial intelligence, and more specifically to a method for diagnosing cancer and predicting the type of cancer based on artificial intelligence by extracting nucleic acids from a biological sample to obtain sequence information, generating vectorized data based on the aligned reads, and analyzing a calculated value obtained by inputting the vectorized data to a trained artificial intelligence model.

BACKGROUND ART

Cancer diagnosis in clinical practice is usually performed by tissue biopsy after history examination, physical examination, and clinical evaluation. Cancer diagnosis based on clinical trials is possible only when the number of cancer cells is 1 billion or more and the diameter of the cancer is 1 cm or more. In this case, cancer cells already have the potential to metastasize and at least half thereof have already metastasized. In addition, tissue biopsy is invasive, which disadvantageously causes patients considerable discomfort and is often incompatible with cancer therapy. Further, tumor markers for monitoring substances produced directly or indirectly from cancer are used in cancer screening. However, the tumor markers have limited accuracy because more than half of tumor marker screening results indicate normal even in the presence of cancer and tumor marker screening results often indicate positive even in the absence of cancer.

Recently, in response to the requirements for cancer diagnosis methods, such as relative ease, non-invasiveness, high sensitivity and high specificity, liquid biopsy using bodily fluids from patients has been widely used for cancer diagnosis and follow-up examination. Liquid biopsy is a non-invasive diagnostic method that is attracting great attention as an alternative to conventional invasive diagnosis and examination methods. However, there are no results of large-scale research confirming the effects of liquid biopsy as a method for diagnosing cancer, and there are no results of research on the diagnosis of ambiguous cancer or the differentiation of ambiguous cancer types through liquid biopsy.

Significant research efforts have been devoted to cancer diagnosis and treatment to mitigate the effects of cancer on health. In particular, SMCT (somatic mutation-based cancer typing) is one of the most important research issues. SMCT enables treatment planning depending on the cancer type/subtype determined based on the somatic genetic mutations of patients. A recent decrease in the cost of DNA sequencing has brought about a rapid increase in DNA sequencing data and thus great promotion of the development of SMCT. Unlike conventional cancer typing methods, which are generally based on the tumor's morphological appearance or gene expression levels (i.e., mRNA profiles or protein profiles), SMCT can distinguish tumors with similar histopathological appearance, thus reflecting the cancer microenvironment better and being advantageous in providing results of accurate carcinoma classification (Sun, Y. et al. Sci Rep Vol. 9, 17256, 2019).

Recently, methods of predicting the type of cancer using three-dimensional structures of chromosome or copy number abnormalities in addition to SMCT have been reported (Yuan et al. BMC Genomics, Vol. 19(Suppl 6), pp. 565, 2018, 10-2019-0036494).

Meanwhile, research to apply the efficient pattern recognition method possessed by humans to actual computers is being actively conducted as a solution to the problem of classifying input patterns frequently encountered in the engineering field into specific groups.

Among a lot of computer-based research, there is research on artificial neural networks obtained by modelling, in an engineering manner, the human brain cellular structure where efficient pattern recognition occurs. To solve the problem of classifying input patterns into specific groups, artificial neural networks use algorithms that mimic the learning ability of humans. Through this algorithm, the artificial neural network can create a mapping between the input pattern and the output pattern, which is expressed as the artificial neural network having the ability to learn. In addition, the artificial neural network has the ability to generalize so that it can generate a relatively correct output for an input pattern that is not used for learning based on the trained result. Because of the two typical performances of learning and generalization, artificial neural networks are being applied to problems that are difficult to solve using conventional sequential programming methods. The artificial neural network has a wide range of uses and is actively applied to fields such as pattern classification, continuous mapping, non-linear system identification, non-linear control, and robot control.

Meanwhile, artificial neural networks are computational models implemented in software or hardware that mimic the computational ability of biological systems using a large number of artificial neurons connected via connective lines. Artificial neural networks use artificial neurons, which represent the functions of biological neurons in simplified form. Artificial neural networks conduct human cognition or learning processes by interconnecting the artificial neurons through connective lines having respective connection intensities. The term "connection intensity", which is interchangeable with "connection weight", refers to a predetermined value of the connection line. Artificial neural network learning may be classified into supervised learning and unsupervised learning. Supervised learning is a method of providing input data and output data corresponding thereto to a neural network and updating the connection intensities of connecting lines so that output data corresponding to the input data is output. Representative learning algorithms include delta rule and back propagation learning. Unsupervised learning is a method in which an artificial neural network independently learns connection intensities using only input data, without a target value. Unsupervised learning updates connection weights based on correlations between input patterns.

Applying large amounts of data to machine learning causes the so-called "curse of dimensionality" problem due to the increased complexity and the greater number of dimensions. In other words, as the number of dimensions of the required data approaches infinity, the distance between any two points also approaches infinity, and the amount of data, that is, the density, becomes lower in high-dimensional space, which makes it impossible to properly reflect the features of the data (Richard Bellman, Dynamic Programming, 2003, chapter 1). Recently developed deep learning has a structure in which a hidden layer is present between an input layer and an output layer, and has been reported to greatly improve the performance of the classifier in high-dimensional data such as images, videos, and signal data by processing a linear combination of variable values transmitted from the input layer with nonlinear functions (Hinton, Geoffrey, et al., IEEE Signal Processing Magazine Vol. 29.6, pp. 82-97, 2012).

Various patents (KR 10-2017-0185041, KR 10-2017-0144237, and KR 10-2018-124550) describe the use of artificial neural networks in biological fields, but there is a lack of research on methods for predicting cancer types through artificial neural network analysis based on sequencing information of cell-free DNA (cfDNA).

Accordingly, as a result of extensive and earnest efforts to solve the above problems and develop a method for diagnosing cancer and predicting a cancer type based on artificial intelligence with high sensitivity and accuracy, the present inventors found that cancer diagnosis and cancer type prediction can be realized with high sensitivity and accuracy by generating vectorized data based on reads aligned with chromosomal regions and analyzing the data using a trained artificial intelligence model, and the present invention has been completed based on this finding.

DISCLOSURE

Therefore, it is one object of the present invention to provide a method for diagnosing cancer and predicting the type of cancer based on artificial intelligence.

It is another object of the present invention to provide a device for diagnosing cancer and predicting the type of cancer based on artificial intelligence.

It is another object of the present invention to provide a computer-readable storage medium including instructions configured to be executed by a processor for diagnosing cancer and predicting the type of cancer by the method described above.

In accordance with one aspect of the present invention, the above and other objects can be accomplished by the provision of a method of providing information to diagnose cancer and predict the type of cancer based on artificial intelligence, the method including (a) extracting nucleic acids from a biological sample to obtain sequence information, (b) aligning the sequence information (reads) with a reference genome database, (c) generating vectorized data using nucleic acid fragments based on the aligned sequence information (reads), (d) inputting the generated vectorized data to a trained artificial intelligence model, analyzing the resulting output value, and comparing the resulting output value with a cut-off value to determine whether there is cancer, and (e) predicting the type of cancer through comparison of the output value.

In accordance with another aspect of the present invention, provided is a method of diagnosing cancer and predicting the type of cancer based on artificial intelligence, the method including (a) extracting nucleic acids from a biological sample to obtain sequence information, (b) aligning the sequence information (reads) with a reference genome database, (c) generating vectorized data using nucleic acid fragments based on the aligned sequence information (reads), (d) inputting the generated vectorized data into a trained artificial intelligence model, analyzing the resulting output value, and comparing the resulting output value with a cut-off value to determine whether or not there is cancer, and (e) predicting the type of cancer through comparison of the output value.

In accordance with another aspect of the present invention, provided is a device for diagnosing cancer and predicting the type of cancer based on artificial intelligence, the device including a decoder configured to extract nucleic acids from a biological sample and decode sequence information, an aligner configured to align the decoded sequence with a reference genome database, a data generator configured to generate vectorized data using nucleic acid fragments based on aligned sequence information (reads), a cancer diagnostic unit configured to input the generated vectorized data to a trained artificial intelligence model, analyze the data, and compare the resulting value with a cut-off value to thereby determine whether or not cancer is present, and a cancer type predictor to analyze the output result and thereby predict the type of cancer.

In accordance with another aspect of the present invention, provided is a computer-readable storage medium including an instruction configured to be executed by a processor for diagnosing cancer and predicting the type of cancer through the following steps including (a) extracting nucleic acids from a biological sample to obtain sequence information, (b) aligning the obtained sequence information (reads) with a reference genome database, (c) generating vectorized data using nucleic acid fragments based on the aligned sequence information (reads), (d) inputting the generated vectorized data into a trained artificial intelligence model, analyzing the resulting output value, and comparing the resulting output value with a cut-off value to determine whether or not there is cancer, and (e) predicting the type of cancer through comparison of the output value.

BEST MODEL

Unless defined otherwise, all technical and scientific terms used herein have the same meanings as appreciated by those skilled in the field to which the present invention pertains. In general, the nomenclature used herein is well-known in the art and is ordinarily used.

It was found in the present invention that diagnosis of cancer and prediction of cancer type are possible with high sensitivity and accuracy by aligning sequencing data obtained from a sample with a reference genome, generating vectorized data based on the aligned nucleic acid fragments, calculating a DPI using a trained artificial intelligence model, and performing analysis.

Figure 1:
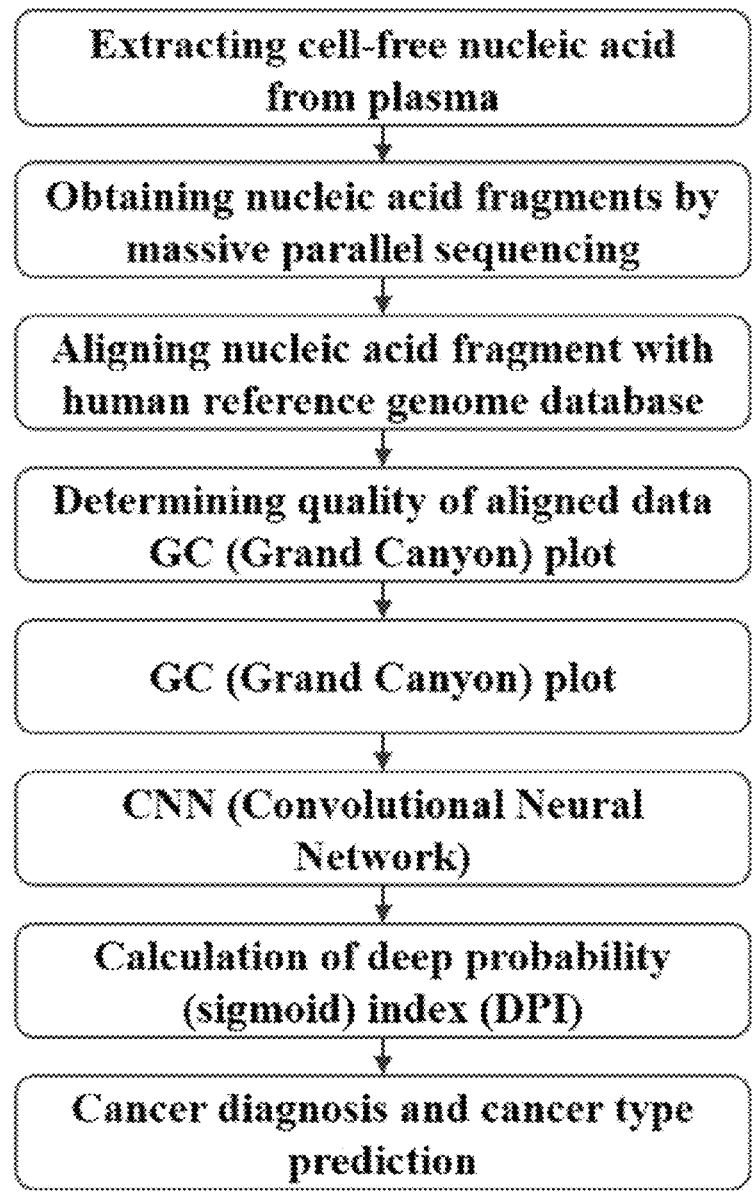
FIG. 1 is an overall flowchart for determining a chromosomal abnormality based on artificial intelligence according to the present invention.

That is, in one embodiment of the present invention, developed is a method including sequencing DNA extracted from blood, aligning the sequencing data with a reference genome, calculating the distance between nucleic acid fragments or amount of the nucleic acid fragments in each predetermined chromosomal bin, generating vectorized data with the chromosomal bin on the X-axis and the distance between nucleic acid fragments or amount thereof on the Y-axis, training a deep-learning model for it to calculate a DPI, comparing the DPI with a cut-off value to determine as to whether or not cancer develops, and determining a type of cancer showing the highest DPI among the calculated DPIs for respective cancer types as the cancer type of the sample (FIG. 1).

In one aspect, the present invention is directed to a method of providing information to diagnose cancer and predict the type of cancer based on artificial intelligence, the method including:
 (a) extracting nucleic acids from a biological sample to obtain sequence information;
 (b) aligning the sequence information (reads) with a reference genome database;
 (c) generating vectorized data using nucleic acid fragments based on the aligned sequence information (reads);
 (d) inputting the generated vectorized data to a trained artificial intelligence model, analyzing the resulting output value, and comparing the resulting output value with a cut-off value to determine whether or not there is cancer; and
 (e) predicting the type of cancer through comparison of the output value.

In the present invention, any nucleic acid fragment can be used without limitation, as long as it is a fragment of a nucleic acid extracted from a biological sample, and the nucleic acid fragment is preferably a fragment of a cell-free nucleic acid or an intracellular nucleic acid, but is not limited thereto.

In the present invention, the nucleic acid fragment may be obtained by direct sequencing, next-generation sequencing, or sequencing through non-specific whole genome amplification.

In the present invention, the nucleic acid fragment may mean a read when next-generation sequencing is used.

In the present invention, the cancer may be a solid cancer or a blood cancer, and is preferably selected from the group consisting of non-Hodgkin lymphoma, Hodgkin lymphoma, acute-myeloid leukemia, acute-lymphoid leukemia, multiple myeloma, head and neck cancer, lung cancer, glioblastoma, colorectal/rectal cancer, pancreatic cancer, breast cancer, ovarian cancer, melanoma, prostate cancer, thyroid cancer, stomach cancer, gallbladder cancer, biliary tract cancer, bladder cancer, small intestine cancer, cervical cancer, cancer of unknown primary, kidney cancer, and mesothelioma, but the cancer is not limited thereto.

In the present invention,
 step (a) includes:
 (a-i) obtaining nucleic acids from the blood, semen, vaginal cells, hair, saliva, urine, oral cells, amniotic fluid containing placental cells or fetal cells, tissue cells, and a mixture thereof;
 (a-ii) removing proteins, fats, and other residues from the collected nucleic acids using a salting-out method, a column chromatography method, or a bead method to obtain purified nucleic acids;
 (a-iii) producing a single-end sequencing or paired-end sequencing library for the purified nucleic acids or nucleic acids randomly fragmented by an enzymatic digestion, pulverization, or hydroshear method;
 (a-iv) reacting the produced library with a next-generation sequencer; and
 (a-v) obtaining sequence information (reads) of the nucleic acids in the next-generation sequencer.

In the present invention, the next-generation sequencer may be used for any sequencing method known in the art. Sequencing of nucleic acids isolated using the selection method is typically performed using next-generation sequencing (NGS). Next-generation sequencing includes any sequencing method that determines the nucleotide sequence of either each nucleic acid molecule or of a proxy cloned from each nucleic acid molecule so as to be highly similar thereto (e.g., $10^5$ or more molecules are sequenced simultaneously). In one embodiment, the relative abundance of nucleic acid species in the library can be estimated by counting the relative number of occurrences of the sequence homologous thereto in data produced by sequencing experimentation. Next-generation sequencing is known in the art, and is described, for example, in Metzker, M. (2010), Nature Biotechnology Reviews 11:31-46, which is incorporated herein by reference.

In one embodiment, next-generation sequencing is performed to determine the nucleotide sequence of each nucleic acid molecule (using, for example, a HelioScope Gene-Sequencing system from Helicos Biosciences or a PacBio RS system from Pacific Biosciences). In other embodiments, massive parallel short-read sequencing, which produces more bases of the sequence per sequencing unit than other sequencing methods, for example, other sequencing methods that produce fewer but longer reads, determines the nucleotide sequence of a proxy cloned from each nucleic acid molecule (using, for example, a Solexa sequencer from Illumina Inc., located in San Diego, CA; 454 Life Sciences (Branford, Connecticut) and Ion Torrent). Other methods or devices for next-generation sequencing may be provided by 454 Life Sciences (Branford, Connecticut), Applied Biosystems (Foster City, CA; SOLiD Sequencer), Helicos Biosciences Corporation (Cambridge, MA) and emulsion and microfluidic sequencing nanodrops (e.g., GnuBIO Drops), but are not limited thereto.

Platforms for next-generation sequencing include, but are not limited to, the FLX System genome sequencer (GS) from Roche/454, the Illumina/Solexa genome analyzer (GA), the Support Oligonucleotide Ligation Detection (SOLiD) system from Life/APG, the G.007 system from Polonator, the HelioScope gene-sequencing system from Helicos Biosciences, and the PacBio RS system from Pacific Biosciences.

NGS technologies may, for example, include one or more of template production, sequencing, imaging, and data analysis steps.

Template production. Methods for producing templates include randomly disrupting nucleic acids (e.g., genomic DNA or cDNA) into small sizes and producing sequencing templates (e.g., fragment templates or mate-pair templates). Spatially separated templates may be attached or immobilized on a solid surface or support, which allows simultaneous large-scale sequencing reactions to be performed. Examples of types of templates that can be used for NGS reactions include templates amplified from clones derived from single DNA molecules and single DNA molecule templates.

Methods for producing the templates amplified from clones include, for example, emulsion PCR (emPCR) and solid-phase amplification.

EmPCR may be used to produce templates for NGS. Typically, a library of nucleic acid fragments is produced, and adapters containing universal priming sites are ligated to the ends of the fragments. The fragments are then denatured into single strands and captured using beads. Each bead captures a single nucleic acid molecule. After amplification and enrichment of emPCR beads, a large amount of templates can be attached, immobilized to a polyacrylamide gel on a standard microscope slide (from, for example, Polonator) and chemically crosslinked to an amino-coated glass surface (e.g., Life/APG; Polonator), or deposited in individual PicoTiterPlate (PTP) wells (e.g., Roche/454). At this time, an NGS reaction may be performed.

Solid-phase amplification can also be used to produce templates for NGS. Typically, the front and rear primers are covalently attached to the solid support. The surface density of the amplified fragment is defined as the ratio of primer to template on the support. Solid-phase amplification is capable of producing millions of spatially separated template clusters (e.g., Illumina/Solexa). The ends of the template cluster can be hybridized to universal primers for NGS reactions.

Other methods for producing clone-amplified templates include, for example, multiple displacement amplification (MDA) (Lasken R. S.; Curr. Opin. Microbiol. 2007; 10(5): 510-6). MDA is a non-PCR-based DNA amplification method. The reaction involves annealing random hexamer primers to templates and synthesizing DNA using a high-fidelity enzyme, typically 029, at a constant temperature. MDA can yield large-scale products with a lower error frequency.

Template amplification methods such as PCR can bind the NGS platform to the target or enrich specific regions of the genome (e.g., exons). Representative template enrichment methods include, for example, microdroplet PCR (Tewhey R. et al., Nature Biotech. 2009, 27:1025-1031), custom-designed oligonucleotide microarrays (e.g., Roche/Nimble-Gen oligonucleotide microarrays), solution-based hybridization (e.g., molecular inversion probes, MIPs) (Porreca G J et al., Nature Methods, 2007, 4:931-936; Krishnakumar S. et al., Proc. Natl. Acad. Sci. USA, 2008, 105:9296-9310; Turner E H et al., Nature Methods, 2009, 6:315-316), and biotinylated RNA capture sequences (Gnirke A. et al., Nat. Biotechnol. 2009; 27(2):182-9).

Single-molecule templates are another type of template that can be used for NGS reactions. Spatially separated single-molecule templates may be immobilized on a solid support by a variety of methods. In one approach, each primer molecule is covalently attached to a solid support. The adapter is added to the template and the template is then hybridized to the immobilized primer. In another approach, a single-molecule template is covalently attached to a solid support by priming and extending a single-stranded single-molecule template from the immobilized primer. The universal primer is then hybridized to the template. In another approach, a single polymerase molecule is attached to a solid support to which a primed template is bound.

Sequencing and imaging. Representative sequencing and imaging methods for NGS include, but are not limited to, cyclic reversible termination (CRT), sequencing by ligation (SBL), pyrosequencing, and real-time sequencing.

CRT uses reversible terminators in a cyclic method that includes, at a minimum, steps of nucleotide incorporation, fluorescence imaging, and cleavage. Typically, a DNA polymerase incorporates a single fluorescently modified nucleotide complementary to the complementary nucleotide of the template base in the primer. DNA synthesis is terminated after incorporation of a single nucleotide, and the unincorporated nucleotides are washed out. Imaging is performed to determine the homology of the incorporated labeled nucleotides. Then, in the cleavage step, the terminator/inhibitor and the fluorescent dye are removed. Representative NGS platforms using the CRT method include, but are not limited to, Illumina/Solexa Genome Analyzer (GA), which uses a clone-amplification template method combined with a 4-color CRT method involving detection using total internal reflection fluorescence (TIRF); and Helicos Biosciences/HelioScope, using a single-molecule template method combined with a 1-color CRT method involving detection using TIRF.

SBL uses a DNA ligase and either a 1-base-encoded probe or a 2-base-encoded probe for sequencing.

Typically, a fluorescently labeled probe is hybridized to a complementary sequence adjacent to the primed template. DNA ligases are used to ligate dye-labeled probes to primers. After the non-ligated probes are washed, fluorescence imaging is performed to determine the identity of the ligated probes. The fluorescent dye may be removed using a cleavable probe that regenerates the 5'-PO4 group for subsequent ligation cycles. Alternatively, new primers may be hybridized to the template after old primers have been removed. Representative SBL platforms include, but are not limited to, Life/APG/SOLiD (support oligonucleotide ligation detection), which uses a two-base-encoded probe.

The pyrosequencing method is based on detection of activity of DNA polymerase with another chemiluminescent enzyme. Typically, this method includes sequencing a single strand of DNA by synthesizing complementary strands of one base pair at a time and detecting the base that is actually added at each step. The template DNA is stationary, and solutions of A, C, G, and T nucleotides are sequentially added and removed during the reaction. Light is generated only when the nucleotide solution replenishes the unpaired base of the template. The sequence of the solution generating the chemiluminescent signal is used to determine the sequence of the template. Representative pyrosequencing platforms include, but are not limited to, those from Roche/454, using DNA templates produced from 1 to 2 million beads deposited in PTP wells by emPCR.

Real-time sequencing involves imaging the continuous incorporation of dye-labeled nucleotides during DNA synthesis. Representative real-time sequencing platforms include, but are not limited to, a platform from Pacific Biosciences, which uses DNA polymerase molecules attached to the surface of respective zero-mode waveguide (ZMW) detectors to obtain sequence information when phosphate-linked nucleotides are incorporated in the growing primer strands;

the Life/VisiGen platform using genetically engineered DNA polymerases along with attached fluorescent dyes to create an enhanced signal after incorporation of the nucleotide by fluorescence resonance energy transfer (FRET); and a platform from LI-COR Biosciences using dye-quencher nucleotides in sequencing reactions.

Other NGS methods include, but are not limited to, nanopore sequencing, sequencing by hybridization, nano-transistor-array-based sequencing, Polony sequencing, scanning tunneling microscopy (STM)-based sequencing, and nanowire molecular sensor-based sequencing.

Nanopore sequencing involves electrophoresis of nucleic acid molecules in solution through nano-scale pores that provide a highly airtight area for analysis of single-nucleic-acid polymers. Representative nanopore sequencing methods are described in Branton D. et al., Nat. Biotechnol. 2008; 26(10):1146-53] and elsewhere.

Sequencing by hybridization is a non-enzymatic method using DNA microarrays. Typically, a single pool of DNA is fluorescently labeled and hybridized into an array containing a known sequence. The hybridization signal from a given spot on the array can be used to identify the DNA sequence. Binding of one strand of DNA to another strand complementary thereto in a DNA double strand is sensitive even to single-base mismatches when the hybrid region is short or when a specified mismatch detection protein is present. Representative hybridization sequencing methods are described, for example, in Hanna G. J. et al., J. Clin. Microbiol. 2000; 38(7): 2715-21; and Edwards J. R. et al., Mut. Res. 2005; 573(1-2): 3-12.

Polony sequencing is based on Polony amplification and multiple single-base-extension (FISSEQ). Polony amplification is a method of amplifying DNA in situ on a polyacrylamide film. Representative Polony sequencing methods are described, for example, in US Patent Application Publication No. 2007/0087362.

Nanotransistor-array-based devices such as carbon nanotube field effect transistors (CNTFETs) can also be used for NGS. For example, DNA molecules are extended and driven across nanotubes by microfabricated electrodes. DNA molecules sequentially contact the carbon nanotube surface, and a difference in current flow from the respective bases is created due to charge transfer between the DNA molecule and the nanotube. DNA is sequenced by recording the difference. Representative nanotransistor-array-based sequencing methods are described, for example, in US Patent Publication No. 2006/0246497.

Scanning tunneling microscopy (STM) can also be used for NGS. Using a piezoelectrically controlled probe that performs a raster scan of the specimen, STM forms an image on the surface thereof. STM can be used to image the physical properties of single DNA molecules, causing coherent electron tunneling imaging and spectroscopy, for example, by integrating a flexible actuator-driven gap with a scanning tunneling microscope. Representative sequencing methods using STM are described, for example, in US Patent Application Publication No. 2007/0194225.

Molecular analysis devices consisting of nanowire-molecular sensors can also be used for NGS. Such devices can detect the interaction of nitrogenous substances disposed on nucleic acid molecules and nanowires such as DNA. Molecular guides are disposed to guide molecules near the molecular sensors to allow interaction and subsequent detection. Representative sequencing methods using nanowire molecular sensors are described, for example, in US Patent Application Publication No. 2006/0275779.

Double-stranded sequencing may be used for NGS. Double-stranded sequencing uses blocking and unblocking primers to sequence both the sense and antisense strands of DNA. Typically, this method includes: annealing an unblocking primer to a first strand of a nucleic acid; annealing a second blocking primer to a second strand of the nucleic acid; extending the nucleic acid along the first strand with a polymerase; terminating the first sequencing primer; deblocking the second primer; and extending the nucleic acid along the second strand. Representative double-stranded sequencing methods are described, for example, in U.S. Pat. No. 7,244,567.

Data analysis stage.

After NGS reads are formed, they are aligned or de novo assembled to a known reference sequence.

For example, identification of genetic modifications such as single-nucleotide polymorphisms and structural variants in a sample (e.g., a tumor sample) can be performed by aligning NGS reads to a reference sequence (e.g., a wild-type sequence). A method of aligning NGS reads to sequences is described, for example, in Trapnell C. and Salzberg S. L. Nature Biotech., 2009, 27:455-457.

Examples of de novo assembly are described, for example, in Warren R. et al., Bioinformatics, 2007, 23:500-501; Butler J. et al., Genome Res., 2008, 18:810-820; and Zerbino D. R. and Birney E., Genome Res., 2008, 18:821-829.

Sequence alignment or assembly can be performed using read data from one or more NGS platforms, for example, by mixing Roche/454 and Illumina/Solexa read data. In the present invention, the alignment may be performed using the BWA algorithm and the hg19 sequence, but is not limited thereto.

In the present invention, the sequence alignment of step (b) includes a computational method or approach using a computer algorithm to determine the case where there is the possibility that a sequence (e.g., a short-read sequence obtained, for example, through next-generation sequencing) is derived from the genome or the case where there is identity therebetween by evaluating the similarity between a read sequence and a reference sequence. Various algorithms may be applied to the sequence alignment problem. Some algorithms are relatively slow, but enable relatively high specificity. These include, for example, dynamic-programming-based algorithms. Dynamic programming is a method of solving complicated problems by segmenting them into simpler steps. Other approaches are more efficient, but are typically not exhaustive, and include, for example, heuristic algorithms and probabilistic methods designed for massive database searches.

Typically, the alignment process may include two steps, namely candidate screening and sequence alignment. Candidate screening reduces the search space for sequence alignments from the entire genome in order to obtain a shorter list of possible alignment positions. As the term literally implies, sequence alignment includes aligning sequences including the sequences obtained during candidate screening. This may be performed using broad alignment (e.g., Needleman-Wunsch alignment) or local alignment (e.g., Smith-Waterman alignment).

Most attribute sorting algorithms may have one of three types based on the indexing method: algorithms based on hash tables (e.g. BLAST, ELAND, SOAP), suffix trees (e.g. Bowtie, BWA), and merge sort (for example, slider). Short read sequences are typically used for alignment. Examples of sequence alignment algorithms/programs for short-read sequences include, but are not limited to, BFAST (Homer N. et al., PLoS One. 2009; 4(11):e7767), BLASTN (from blast.ncbi.nlm.nih.gov on the world wide web), BLAT (Kent W. J. Genome Res. 2002; 12(4):656-64), Bowtie (Langmead B. et al., Genome Biol. 2009; 10(3):R25), BWA (Li H. and Durbin R., Bioinformatics, 2009, 25:1754-60), BWA-SW (Li H. and Durbin R., Bioinformatics, 2010; 26(5):589-95), CloudBurst (Schatz M. C., Bioinformatics, 2009; 25(11): 1363-9), Corona Lite (Applied Biosystems, Carlsbad, California, USA), CASHX (Fahlgren N. et al., RNA, 2009; 15, 992-1002), CUDA-EC (Shi H. et al., J. Comput. Biol. 2010; 17(4):603-15), ELAND (bioit.dbi.udel.edu/howto/eland on the world wide web), GNUMAP (Clement N. L. et al., Bioinformatics. 2010; 26(1):38-45), GMAP (Wu T. D. and Watanabe C. K., Bioinformatics, 2005; 21(9):1859-75), GSNAP (Wu T. D. and Nacu S., Bioinformatics, 2010; 26(7):873-81), Geneious Assembler (Biomatters Ltd., Oakland, New Zealand), LAST, MAQ (Li H. et al., Genome Res. 2008; 18(11):1851-8), Mega-BLAST (at ncbi.nlm.nih.gov/blast/megablast.shtml on the world wide web), MOM (Eaves H. L. and Gao Y. Bioinformatics. 2009; 25(7):969-70), MOSAIK (at bioinformatics.bc.edu/marthlab/Mosaik on the world wide web), NovoAlign (at novocraft.com/main/index.php on the world wide web), PALMapper (at fml.tuebingen.mpg.de/raetsch/suppl/palmapper on the world wide web), PASS (Campagna D. et al., Bioinformatics, 2009; 25(7):967-8), PatMaN (Prufer K. et al., Bioinformatics, 2008; 24(13):1530-1), PerM (Chen Y. et al., Bioinformatics, 2009, 25 (19): 2514-2521), ProbeMatch (Kim Y. J. et al., Bioinformatics. 2009; 25(11):1424-5), QPalma (de Bona F. et al., Bioinformatics, 2008, 24(16): i174), RazerS (Weese D. et al., Genome Research, 2009, 19:1646-1654), RMAP (Smith A. D. et al., Bioinformatics, 2009; 25(21): 2841-2), SeqMap (Jiang H. et al., Bioinformatics, 2008; 24:2395-2396), Shrec (Salmela L., Bioinformatics, 2010; 26(10):1284-90), SHRiMP (Rumble S. M. et al., PLoS Comput. Biol., 2009, 5(5):e1000386), SLIDER (Malhis N. et al., Bioinformatics, 2009, 25 (1): 6-13), SLIM Search (Muller T. et al., Bioinformatics, 2001; 17 Suppl 1:S182-9), SOAP (Li R. et al., Bioinformatics, 2008; 24(5):713-4), SOAP2 (Li R. et al., Bioinformatics, 2009; 25(15):1966-7), SOCS (Ondov B. D. et al., Bioinformatics, 2008; 24(23): 2776-7), SSAHA (Ning Z. et al., Genome Res. 2001; 11(10): 1725-9), SSAHA2 (Ning Z. et al., Genome Res. 2001; 11(10):1725-9), Stampy (Lunter G. and Goodson M., Genome Res. 2010, epub ahead of print), Taipan (at taipan.sourceforge.net on the world wide web), UGENE (at ugene.unipro.ru on the world wide web), XpressAlign (at bcgsc.ca/platform/bioinfo/software/XpressAlign on the world wide web), and ZOOM (Bioinformatics Solutions Inc., Waterloo, Ontario, Canada).

A sequence alignment algorithm may be selected based on a number of factors including, for example, the sequencing technique, length of reads, number of reads, available computing resources, and sensitivity/scoring requirements. Different sequence alignment algorithms can achieve different levels of speed, alignment sensitivity, and alignment specificity. Alignment specificity refers to the percentage of target sequence residues that are correctly aligned with the predicted alignment, as typically shown in the submission. Alignment sensitivity also refers to the percentage of target sequence residues that are aligned, as shown in typically predicted alignments in the submission.

Alignment algorithms such as ELAND or SOAP can be used to align short reads (e.g., from Illumina/Solexa sequencers) to a reference genome when speed is the first factor to be considered. Alignment algorithms such as BLAST or Mega-BLAST are used to determine similarity using shorter reads (e.g., Roche FLX) when specificity is considered the most important factor, although these methods are slower. Alignment algorithms such as MAQ or NovoAlign can be used for single- or paired-end data when the quality score is important and accuracy is thus essential (e.g. in fast massive SNP searches). Alignment algorithms such as Bowtie or BWA use the Burrows-Wheeler Transform (BWT) and thus require a relatively small memory footprint. Alignment algorithms such as BFAST, PerM, SHRiMP, SOCS, or ZOOM map color space reads and thus can be used along with the SOLiD platform from ABI. In some applications, results from two or more sorting algorithms may be combined.

In the present invention, the length of the sequence information (reads) in step (b) is 5 to 5,000 bp, and the number of sequence information (reads) that are used may be 5,000 to 5 million, but the invention is not limited thereto.

In the present invention, as the vectorized data in step (c), any vectorized data that can be generated using aligned reads-based nucleic acid fragments may be used without limitation, but the vectorized data is preferably a grand canyon plot (GC plot), but is not limited thereto.

In the present invention, the vectorized data is preferably an image, but is not limited thereto. An image is basically composed of pixels. If an image composed of pixels is vectorized, it may be expressed as a monochromatic 2D vector (black and white), a three-channel 2D vector (RGB colors), or a four-channel 2D vector (CMYK colors) depending on the type of image.

The vectorized data of the present invention is not limited to image data, and, for example, may be input data of an artificial intelligence model using an n-channel 2D vector (multi-channel vector) created by stacking n black-and-white images.

In the present invention, the GC plot is a plot created by taking a specific section (either a constant bin or a bin of a different size) on the X-axis, and taking numerical values that can be expressed in terms of nucleic acid fragments, such as the distance between nucleic acid fragments or count of the nucleic acid fragments, on the Y-axis. In the present invention, the bin may be 1 kbp to 10 Mbp, but is not limited thereto.

In the present invention, the method may further include, prior to step (c), separating nucleic acid fragments satisfying a mapping quality score from the aligned nucleic acid fragments.

In the present invention, the mapping quality score may vary depending on a desired criterion, but is preferably 15 to 70, more preferably 50 to 70, and most preferably 60.

In the present invention, the GC plot of step (c) is characterized in that the vectorized data is generated by calculating a distribution of aligned nucleic acid fragments in each chromosome bin based on the count of nucleic acid fragments in each bin or the distance between the nucleic acid fragments.

Vectorization of the calculated count of nucleic acid fragments or the calculated distance between nucleic acid fragments in the present invention may be performed using any known method for vectorizing the calculated value without limitation.

In the present invention, calculating the distribution of the aligned sequence information in each chromosome bin based on the count of nucleic acid fragments may be performed using a process including the following steps:
  i) dividing chromosomes into predetermined bins;
  ii) determining the count of nucleic acid fragments that are aligned in each bin;
  iii) dividing the determined count of nucleic acid fragments in each bin by the total number of nucleic acid fragments in the sample to conduct normalization; and
  iv) creating a GC plot with the order of respective bins on the X-axis and the normalized value calculated in step iii) on the Y-axis.

In the present invention, calculating the distribution of the aligned sequence information in each chromosome bin based on the distance between nucleic acid fragments may be performed using a process including the following steps:
i) dividing chromosomes into predetermined bins;
ii) determining the distance between nucleic acid fragments (fragment distance, FD) aligned in each bin;
iii) determining a representative distance between fragments (RepFD) of each bin based on the fragment distance calculated for each bin;
iv) dividing the representative distance between fragments (RepFD) calculated in step iii) by a representative total nucleic acid fragment distance to conduct normalization; and
v) creating a GC plot with the order of respective bins on the X-axis and the normalized value calculated in step iv) on the Y-axis.

In the present invention, the predetermined bin may be 1 Kbp to 3 Gbp, but is not limited thereto.

In the present invention, the method may further include grouping the nucleic acid fragments. The grouping may be performed based on the adapter sequence of the aligned nucleic acid fragments. The distance between the nucleic acid fragments for the selected sequence information may be calculated separately for nucleic acid fragments aligned in a forward direction and nucleic acid fragments aligned in a reverse direction.

In the present invention, the FD is defined as the distance between the reference value of the $i^{th}$ nucleic acid fragment and the reference value of at least one nucleic acid fragment selected from the $i+1^{th}$ to the $n^{th}$ nucleic acid fragments, among the obtained n nucleic acid fragments.

In the present invention, the FD may be one or more values selected from the group consisting of the sum, difference, product, mean, log of product, log of sum, median, quantile, minimum, maximum, variance, standard deviation, median absolute deviation and coefficient of variance of the distance between the reference value of the $1^{st}$ nucleic acid fragment and the reference value of at least one nucleic acid fragment selected from the group consisting of the $2^{nd}$ to $n^{th}$ nucleic acid fragments, among the obtained n nucleic acid fragments, and/or one or more reciprocals thereof, values calculated in consideration of weights, and statistical values, but the present invention is not limited thereto.

As used herein, the expression "one or more values . . . and/or one or more reciprocals thereof" is intended to mean that one of the numerical values described above or a combination of two or more thereof may be used.

As used herein, the expression "reference value of the nucleic acid fragment" may be a value obtained by adding an arbitrary value to the median of the nucleic acid fragments or subtracting the arbitrary value therefrom.

The FD for the obtained n nucleic acid fragments may be defined as follows.

$$FD=\text{Dist}(Ri \sim Rj)(1 \le i < j \le n),$$

wherein the Dist function calculates one or more values selected from the group consisting of the sum, difference, product, mean, log of product, log of sum, median, quantile, minimum, maximum, variance, standard deviation, median absolute deviation, and coefficient of variance of the differences between the alignment position values of all nucleic acid fragments between the two nucleic acid fragments Ri and Rj, and/or one or more reciprocals thereof, values calculated in consideration of weights, and statistical values, but is not limited thereto.

That is, as used herein, the FD (fragment distance) refers to the distance between aligned nucleic acid fragments. Here, the number of cases where nucleic acid fragments are selected for distance calculation may be defined as follows. When a total of N nucleic acid fragments is present, the number of combinations of distances between nucleic acid fragments is $$\sum_{k=1}^{n-1} k.$$

That is, when i is 1, i+1 is 2, and the FD may be defined as the distance between the $1^{st}$ nucleic acid fragment and one or more nucleic acid fragments selected from the $2^{nd}$ to $n^{th}$ nucleic acid fragments.

In the present invention, the FD may be obtained by calculating the distance between a specific position inside the $i^{th}$ nucleic acid fragment and a specific position inside at least one of the $i+1^{th}$ to $n^{th}$ nucleic acid fragments.

For example, if a nucleic acid fragment has a length of 50 bp and is aligned at position 4,183 on chromosome 1, the genetic position values that can be used to calculate the distance between this nucleic acid fragment and another nucleic acid fragment are 4,183 and 4,232 on chromosome 1.

If a nucleic acid fragment having a length of 50 bp adjacent to the nucleic acid fragment is aligned at position 4,232 of chromosome 1, the genetic position values that can be used to calculate the distance between this nucleic acid fragment and another nucleic acid fragment are 4,232 and 4,281 of chromosome 1, and the FD between the two nucleic acid fragments is 1 to 99.

If another adjacent 50 bp nucleic acid fragment is aligned at position 4123 of chromosome 1, the genetic position values that can be used to calculate to calculate the distance between this nucleic acid fragment and another nucleic acid fragment are 4,123 and 4,172 of chromosome 1, the FD between the two nucleic acid fragments is 61 to 159, and the FD between the nucleic acid fragment and the first exemplary nucleic acid fragment is 12 to 110, the FD may be one or more selected from the group consisting of the sum, difference, product, mean, log of product, log of sum, median, quantile, minimum, maximum, variance, standard deviation, median absolute deviation and coefficient of variance of one within the range between the two FD values, and/or one or more reciprocals thereof, values calculated in consideration of weights, and statistical values, but are not limited thereto, and is preferably the reciprocal of one within the range of the two FD values, but is not limited thereto.

Preferably, in the present invention, the FD may be a value obtained by adding an arbitrary value to the median of the nucleic acid fragment or subtracting the arbitrary value therefrom.

In the present invention, the median of FD means the most centrally located value when the calculated FDs are arranged in order of size. For example, when there are three values, namely 1, 2, and 100, 2, which is central, is the median. If there is an even number of FDs, the median is determined as the mean of the two middle values. For example, if there are FDs of 1, 10, 90, and 200, the median is 50, which is the mean of 10 and 90.

In the present invention, the arbitrary value can be set without limitation, as long as it can be used to indicate the position of the nucleic acid fragment, but is preferably 0 to 5 kbp or 0 to 300% of the length of the nucleic acid fragment, 0 to 3 kbp or 0 to 200% of the length of the nucleic acid fragment, or 0 to 1 kbp or 0 to 100% of the length of the nucleic acid fragment, more preferably 0 to 500 bp or 0 to 50% of the length of the nucleic acid fragment, but is not limited thereto.

In the present invention, in paired-end sequencing, the FD may be derived based on position values of forward and reverse reads.

For example, if, in a pair of 50-bp-long paired-end reads, the forward read is aligned at position 4183 of chromosome 1 and the reverse read is aligned at position 4349, both ends of this nucleic acid fragment are at positions 4183 and 4349, and reference values that can be used to calculate the nucleic acid fragment distance are 4183 and 4349. At this time, if, in another paired-end read pair adjacent to the nucleic acid fragment, the forward read is aligned at position 4349 of chromosome 1 and the reverse read is aligned at position 4515, the position values of the nucleic acid fragment are 4349 and 4515. The distance between the two nucleic acid fragments may be 0 to 333, and most preferably may be 166, which is the distance corresponding to the median of the respective nucleic acid fragments.

In the present invention, when sequence information is obtained through paired-end sequencing, the method may further include excluding nucleic acid fragments having a mapping quality score below a reference value from the calculation process.

In the present invention, in single-end sequencing, the FD may be derived based on one type of position value among forward and reverse reads.

In the present invention, in the single-end sequencing, if a position value is derived based on sequence information aligned in the forward direction, an arbitrary value is added thereto, and if a position value is derived based on sequence information aligned in the reverse direction, an arbitrary value is subtracted. The arbitrary value may be set without limitation, as long as the FD clearly indicates the position of the nucleic acid fragment, but is preferably 0 to 5 kbp or 0 to 300% of the length of the nucleic acid fragment, 0 to 3 kbp or 0 to 200% of the length of the nucleic acid fragment, or 0 to 1 kbp or 0 to 100% of the length of the nucleic acid fragment, more preferably 0 to 500 bp or 0 to 50% of the length of the nucleic acid fragment, but is not limited thereto.

Nucleic acids to be analyzed in the present invention may be sequenced and expressed in units called "reads". The reads may be divided into single-end sequencing reads (SE) and paired-end sequencing reads (PE) depending on the sequencing method. An SE-type read is a read obtained by sequencing one of a 5' and 3' end of a nucleic acid molecule to a predetermined length in a random direction, and a PE-type read is a read obtained by sequencing both 5' and 3' ends of a nucleic acid molecule to a predetermined length. It is well known to those skilled in the art that due to this difference, one read is generated from one nucleic acid fragment when sequencing in the SE mode, whereas a pair of two reads is generated from one nucleic acid fragment in the PE mode.

The most ideal method to accurately calculate the distance between nucleic acid fragments includes sequencing nucleic acid molecules from the beginning to the end, aligning the reads, and using the median (center) of the position values of the aligned reads. However, the method faces technical restrictions due to limitations on sequencing technology and the high cost thereof. Therefore, sequencing is performed using a method such as SE or PE. In the PE mode, since the start and end positions of the nucleic acid molecule can be recognized, the exact position (median) of the nucleic acid fragment can be determined through the combination of these values. In the SE mode, since only information on one end of the nucleic acid fragment can be used, there is a limitation on accuracy of calculation of the position (median).

Also, when calculating the distance between nucleic acid molecules using the end information of all reads sequenced (aligned) in both forward and reverse directions, an inaccurate value may be obtained due to the factor of the sequencing direction.

Therefore, for technical reasons related to the sequencing method, the 5' end of the forward read has a small position value and the 3' end of the reverse read has a large position value, compared to the central position value of the nucleic acid molecule. When an arbitrary value (extended bp) is added to the forward read and subtracted from the reverse read, using this feature, a value close to the central position of the nucleic acid molecule can be estimated.

That is, the arbitrary value (extended bp) may vary depending on the sample that is used, and cell-free nucleic acids are known to have an average nucleic acid length of about 166 bp, and thus the arbitrary value (extended bp) thereof is set to about 80 bp. If the experiment is performed using fragmentation (e.g. sonication) equipment, about half of the target length set during the fragmentation process may be set as extended bp.

In the present invention, the representative FD (RepFD) includes at least one selected from the group consisting of a sum, difference, product, mean, median, quantile, minimum, maximum, variance, standard deviation, median absolute deviation, and coefficient of variance of FD and/or a reciprocal thereof, and is preferably a median or mean of FDs or a reciprocal thereof, but is not limited thereto.

In the present invention, the vectorized data may include a plurality of chromosome-specific plots in one image.

In the present invention, any artificial intelligence model may be used without limitation in step (d), as long as it is a model that can learn to distinguish between images for cancer types, and is preferably a deep-learning model.

In the present invention, any artificial intelligence model may be used without limitation, as long as it is an artificial neural network algorithm capable of analyzing vectorized data based on an artificial neural network, and is preferably selected from the group consisting of a convolutional neural network (CNN), a deep neural network (DNN), a recurrent neural network (RNN), and an autoencoder, but is not limited thereto.

In the present invention, the recurrent neural network is selected from the group consisting of a long-short term memory (LSTM) neural network, a gated recurrent unit (GRU) neural network, a vanilla recurrent neural network, and an attentive recurrent neural network.

In the present invention, when the artificial intelligence model is a CNN, the loss function for performing binary classification is represented by Equation 1 below, and the loss function for performing multi-class classification is represented by Equation 2 below.

Equation 1: Binary classification $$\text{loss}(\text{model}(x), y) = -\frac{1}{n}\left[\sum_{i=1}^{n}(y_i \log(\text{model}(x_i)) + (1 - y_i)\log(1 - \text{model}(x_i)))\right]$$

Model ($x_i$)=Artificial intelligence model output in response to $i^{th}$ input
y=Actual label value
n=Number of input data Equation 2: Multi-class classification $$\text{loss}(\text{model}(x), y) = -\frac{1}{n}\sum_{i=1}^{n}\left(\sum_{j=1}^{c}(y_{ij}\log(\text{model}(x_i))_j)\right)$$

Model ($x_i$)$_j$=$j^{th}$ artificial intelligence model output in response to $i^{th}$ input
y=Actual label value
n=Number of input data
c=Number of classes In the present invention, the binary classification means that the artificial intelligence model learns to identify the presence or absence of cancer, and multi-class classification means that the artificial intelligence model learns to distinguish between two or more cancer types.

In the present invention, when the artificial intelligence model is a CNN, learning includes the following steps:
i) classifying the generated GC plot into training, validation, and test data,
wherein the training data is used when the CNN model is trained, the validation data is used for hyper-parameter tuning validation, and the test data is used for performance evaluation after optimal model production; and
ii) constructing an optimal CNN model through hyper-parameter tuning and training; and
iii) comparing the performance of multiple models obtained through hyper-parameter tuning using validation data and determining the model having the best validation data to be the optimal model.

In the present invention, the hyper-parameter tuning is a process of optimizing the values of various parameters (the number of convolution layers, the number of dense layers, the number of convolution filters, etc.) constituting the CNN model. Hyper-parameter tuning is performed using Bayesian optimization and grid search methods.

In the present invention, the internal parameters (weights) of the CNN model are optimized using predetermined hyper-parameters, and it is determined that the model is over-fit when validation loss starts to increase compared to training loss. Training is stopped prior to this determination.

In the present invention, any value resulting from analysis of the input vectorized data by the artificial intelligence model in step (d) may be used without limitation, as long as it is a specific score or real number, and the value is preferably a deep probability index (DPI), but is not limited thereto.

In the present invention, "deep probability index" means a value expressed as a probability value by adjusting the output of artificial intelligence to a scale of 0 to 1 using, for the last layer of the artificial intelligence model, a sigmoid function in the case of binary classification and a SoftMax function in the case of multi-class classification.

In binary classification, training is performed using the sigmoid function such that the DPI is adjusted to 1, provided that cancer develops. For example, when a breast cancer sample and a normal sample are input, training is performed such that the DPI of the breast cancer sample is close to 1.

In multi-class classification, as many DPIs as the number of classes are extracted using the SoftMax function. The sum of the DPIs is adjusted to 1 and training is performed such that the DPI of the cancer type is actually adjusted to 1. For example, provided that there are three classes, namely, breast cancer, liver cancer, and normal group, when a breast cancer sample is input, training is performed to adjust a DPI of the breast cancer class to about 1.

In the present invention, the resulting output value of step (d) is obtained for each cancer type.

In the present invention, the artificial intelligence model is trained to adjust an output value to about 1 if there is cancer and to adjust an output value to about 0 if there is no cancer. Therefore, performance (training, validation, test accuracy) is measured based on a cut-off value of 0.5. In other words, if the output value is 0.5 or more, it is determined that there is cancer, and if it is less than 0.5, it is determined that there is no cancer.

Here, it will be apparent to those skilled in the art that the cut-off value of 0.5 may be arbitrarily changed. For example, in an attempt to reduce false positives, the cut-off value may be set to be higher than 0.5 as a stricter criterion for determining whether or not there is cancer, and in an attempt to reduce false negatives, the cut-off value may be set to be lower than 0.5 as a weaker criterion for determining that there is cancer.

Most preferably, the cut-off value can be set by determining the probability of the DPI by applying unseen data (data containing a solution that is different from solutions during training) using the trained artificial intelligence model.

In the present invention, (e) predicting a cancer type through comparison of the output result includes determining the cancer type showing the highest value among the output result values as the cancer of the sample.

In another aspect, the present invention is directed to a device for diagnosing cancer and predicting the type of cancer based on artificial intelligence, the device including:
a decoder configured to extract nucleic acids from a biological sample and decode sequence information;
an aligner configured to align the decoded sequence with a reference genome database;
a data generator configured to generate vectorized data using nucleic acid fragments based on aligned sequence information (reads);
a cancer diagnostic unit configured to input the generated vectorized data into a trained artificial intelligence model, analyze the data, and compare the resulting value with a cut-off value thereby to determine whether or not cancer is present; and
a cancer type predictor to analyze the output result and thereby predict the type of cancer.

In the present invention, the decoder may include a nucleic acid injector to inject nucleic acid extracted from the independent device and a sequence information analyzer to analyze the sequence information of the injected nucleic acid, preferably an NGS analyzer, but is not limited thereto.

In the present invention, the decoder may receive and decode the sequence information data generated in the independent device.

In the present invention, the vectorized data of the data generator may be a Grand Canyon plot (GC plot).

In the present invention, the GC plot is a plot in which a specific section (either bins with a constant size or bins with different sizes) is set as the X-axis and the value that may be expressed based on the nucleic acid fragment, such as the distance or number between nucleic acid fragments, is set as the Y-axis. In the present invention, the bin may be 1 kbp to 10 Mbp, but is not limited thereto.

In the present invention, the data generator may further include a nucleic acid fragment classifier configured to separately classify nucleic acid fragments satisfying a mapping quality score of the aligned nucleic acid fragments prior to generation of vectorized data.

In the present invention, the mapping quality score may vary depending on a desired criterion, but is preferably 15 to 70, more preferably 50 to 70, and most preferably 60.

In the present invention, the GC plot of the data generator is produced with the data vectorized by calculating the count of nucleic acid fragments in each bin or the distance between the nucleic acid fragments.

Vectorization of the calculated count of nucleic acid fragments or the calculated distance between nucleic acid fragments in the present invention may be performed using any known method for vectorizing the calculated value without limitation.

In the present invention, calculating the distribution of the aligned sequence information in each chromosome bin based on the count of nucleic acid fragments may be performed using a process including the following steps:
  i) dividing chromosomes into predetermined bins;
  ii) determining the count of nucleic acid fragments that are aligned in each bin;
  iii) dividing the determined count of nucleic acid fragments in each bin by the total number of nucleic acid fragments in the sample to conduct normalization; and
  iv) creating a GC plot with the order of respective bins on the X-axis and the normalized value calculated in step iii) on the Y-axis.

In the present invention, calculating the distribution of the aligned sequence information in each chromosome bin based on the distance between nucleic acid fragments may be performed using a process including the following steps:
  i) dividing chromosomes into predetermined bins;
  ii) determining the distance between nucleic acid fragments (fragment distance, FD) aligned in each bin;
  iii) determining a representative distance between fragments (RepFD) of each bin based on the fragment distance calculated for each bin;
  iv) dividing the representative distance between fragments (RepFD) calculated in step iii) by a representative total nucleic acid fragment distance to conduct normalization; and
  v) creating a GC plot with the order of respective bins on the X-axis and the normalized value calculated in step iv) on the Y-axis.

In the present invention, the predetermined bin may be 1 kbp to 3 Gbp, but is not limited thereto.

In the present invention, the method may further include grouping the nucleic acid fragments. The grouping may be performed based on the adapter sequence of the aligned nucleic acid fragments. The distance between the nucleic acid fragments for the selected sequence information may be calculated separately for nucleic acid fragments aligned in a forward direction and nucleic acid fragments aligned in a reverse direction.

In the present invention, the FD is defined as the distance between the reference value of the $i^{th}$ nucleic acid fragment and the reference value of at least one nucleic acid fragment selected from the $i+1^{th}$ to the $n^{th}$ nucleic acid fragments, among the obtained n nucleic acid fragments.

In the present invention, the FD may be one or more values selected from the group consisting of the sum, difference, product, mean, log of product, log of sum, median, quantile, minimum, maximum, variance, standard deviation, median absolute deviation and coefficient of variance of the distance between the reference value of the $1^{st}$ nucleic acid fragment and the reference value of at least one nucleic acid fragment selected from the group consisting of the $2^{nd}$ to $n^{th}$ nucleic acid fragments, among the obtained n nucleic acid fragments, and/or one or more reciprocals thereof, values calculated in consideration of weights, and statistical values, but the present invention is not limited thereto.

As used herein, the expression "one or more values . . . and/or one or more reciprocals thereof" is intended to mean that one of the numerical values described above or a combination of two or more thereof may be used.

As used herein, the expression "reference value of the nucleic acid fragment" may be a value obtained by adding an arbitrary value to the median of the nucleic acid fragments or subtracting the arbitrary value therefrom.

In the present invention, any model may be used as the artificial intelligence model of the cancer diagnostic unit without limitation, as long as it is a model that can learn to distinguish between images for cancer types, and is preferably a deep-learning model.

In the present invention, any artificial intelligence model may be used without limitation, as long as it is an artificial neural network algorithm capable of analyzing vectorized data based on an artificial neural network, and is preferably selected from the group consisting of a convolutional neural network (CNN), a deep neural network (DNN), a recurrent neural network (RNN), and an autoencoder, but is not limited thereto.

In the present invention, the recurrent neural network is selected from the group consisting of a long-short term memory (LSTM) neural network, a gated recurrent unit (GRU) neural network, a vanilla recurrent neural network, and an attentive recurrent neural network.

In the present invention, when the artificial intelligence model is a CNN, the loss function for performing binary classification is represented by Equation 1 below, and the loss function for performing multi-class classification is represented by Equation 2 below.

Equation 1: Binary classification $$\text{loss}(\text{model}(x), y) = -\frac{1}{n}\left[\sum_{i=1}^{n}(y_i\log(\text{model}(x_i)) + (1-y_i)\log(1-\text{model}(x_i)))\right]$$

Model ($x_i$)=Artificial intelligence model output in response to $i^{th}$ input
  y=Actual label value
  n=Number of input data Equation 2: Multi-class classification $$\text{loss}(\text{model}(x), y) = -\frac{1}{n}\sum_{i=1}^{n}\left(\sum_{j=1}^{c}(y_{ij}\log(\text{model}(x_i))_j\right)$$

Model $(x_i)_j$=$j^{th}$ artificial intelligence model output in response to $i^{th}$ input
  y=Actual label value
  n=Number of input data
  c=Number of classes In the present invention, binary classification means that the artificial intelligence model learns to identify the presence or absence of cancer, and multi-class classification means that the artificial intelligence model learns to distinguish between two or more cancer types.

In the present invention, when the artificial intelligence model is a CNN, learning includes the following steps:
i) classifying the generated GC plot into training, validation, and test data,
wherein the training data is used when the CNN model is trained, the validation data is used for hyper-parameter tuning validation, and the test data is used for performance evaluation after optimal model production; and
ii) constructing an optimal CNN model through hyper-parameter tuning and training; and
iii) comparing the performance of multiple models obtained through hyper-parameter tuning using validation data and determining the model having the best validation data to be the optimal model.

In the present invention, the hyper-parameter tuning is a process of optimizing the values of various parameters (the number of convolution layers, the number of dense layers, the number of convolution filters, etc.) constituting the CNN model. The hyper-parameter tuning is performed using Bayesian optimization and grid search methods.

In the present invention, in the training process, the internal parameters (weights) of the CNN model are optimized using predetermined hyper-parameters, and it is determined that the model is over-fit when validation loss starts to increase compared to training loss. Training is stopped prior to this determination.

In the present invention, any value resulting from analysis of the input vectorized data by the artificial intelligence model in the cancer diagnostic unit may be used without limitation, as long as it is a specific score or real number, and the value is preferably a deep probability index (DPI), but is not limited thereto.

In the present invention, "deep probability index" means a value expressed as a probability value by adjusting the output of artificial intelligence to a scale of 0 to 1 using, for the last layer of the artificial intelligence model, a sigmoid function in the case of binary classification and a SoftMax function in the case of multi-class classification.

In binary classification, training is performed using the sigmoid function such that the DPI is adjusted to 1, provided that cancer develops. For example, when a breast cancer sample and a normal sample are input, training is performed such that the DPI of the breast cancer sample is close to 1.

In multi-class classification, as many DPIs as the number of classes are extracted using the SoftMax function. The sum of the DPIs is adjusted to 1 and training is performed such that the DPI of the cancer type is actually adjusted to 1. For example, provided that there are three classes, namely, breast cancer, liver cancer, and normal group, when a breast cancer sample is input, training is performed to adjust a DPI of the breast cancer class to about 1.

In the present invention, the resulting output value of the cancer diagnostic unit is obtained for each cancer type.

In the present invention, the artificial intelligence model is trained to adjust an output value to about 1 if there is cancer and to adjust an output value to about 0 if there is no cancer. Therefore, performance (training, validation, test accuracy) is measured based on a cut-off value of 0.5. In other words, if the output value is 0.5 or more, it is determined that there is cancer, and if it is less than 0.5, it is determined that there is no cancer.

Here, it will be apparent to those skilled in the art that the cut-off value of 0.5 may be arbitrarily changed. For example, in an attempt to reduce false positives, the cut-off value may be set to be higher than 0.5 as a stricter criterion for determining whether or not there is cancer, and in an attempt to reduce false negatives, the cut-off value may be set to be lower than 0.5 as a weaker criterion for determining that there is cancer.

Most preferably, the cut-off value can be set by determining the probability of the DPI by applying unseen data (data containing a solution that is different from solutions during training) using the trained artificial intelligence model.

In the present invention, the cancer type predictor predicts a cancer type through comparison of the output result, and determines the cancer type showing the highest value among the output result values as the cancer of the sample.

In another aspect, the present invention is directed to a computer-readable storage medium including an instruction configured to be executed by a processor for diagnosing cancer and predicting the type of cancer through the following steps including:
(a) extracting nucleic acids from a biological sample to obtain sequence information;
(b) aligning the obtained sequence information (reads) with a reference genome database;
(c) generating vectorized data using nucleic acid fragments based on the aligned sequence information (reads);
(d) inputting the generated vectorized data to a trained artificial intelligence model, analyzing the resulting output value, and comparing the resulting output value with a cut-off value to determine whether or not there is cancer; and
(e) predicting the type of cancer through analysis of the output value.

In the present invention, step (a) may include obtaining previously generated sequence information, wherein the previously generated sequence information is obtained by extracting nucleic acids from a biological sample using an NGS device or the like.

In another aspect, the method according to the present disclosure may be implemented using a computer. In one embodiment, the computer includes one or more processors coupled to a chipset. In addition, a memory, a storage device, a keyboard, a graphics adapter, a pointing device, a network adapter and the like are connected to the chipset. In one embodiment, the performance of the chipset is acquired by a memory controller hub and an I/O controller hub. In another embodiment, the memory may be directly coupled to a processor instead of the chipset. The storage device is any device capable of maintaining data, including a hard drive, compact disc read-only memory (CD-ROM), DVD, or other memory devices. The memory gets involved in data and instructions used by the processor. The pointing device may be a mouse, track ball or other type of pointing device, and is used in combination with a keyboard to transmit input data to a computer system. The graphics adapter presents images and other information on a display. The network adapter is connected to the computer system through a local area network or a long distance communication network. However, the computer used herein is not limited to the above configuration, may not have some configurations, may further include additional configurations, and may also be part of a storage area network (SAN), and the computer of the present invention may be configured to be suitable for the execution of modules in the program for the implementation of the method according to the present invention.

The module used herein may mean a functional and structural combination of hardware to implement the technical idea according to the present invention and software to drive the hardware. For example, it is apparent to those skilled in the art that the module may mean a logical unit of a predetermined code and a hardware resource to execute the predetermined code, and does not necessarily mean a physically connected code or one type of hardware.

The method according to the present invention may be implemented in hardware, firmware, or software or a combination thereof. When the method is implemented in the software, the storage medium includes any medium that stores or transmits data in a form readable by a device such as a computer. For example, the computer readable medium may include a read only memory (ROM), a random access memory (RAM), magnetic disk storage media, optical storage media, a flash memory device and other electrical, optical or acoustic signal transmission media.

In this aspect, the present invention is directed to a computer readable medium including an execution module to execute a processor to perform an operation including the steps according to the present invention described above.

EXAMPLE

Hereinafter, the present invention will be described in more detail with reference to examples. However, it will be obvious to those skilled in the art that these examples are provided only for illustration of the present invention, and should not be construed as limiting the scope of the present invention.

Example 1. Extracting DNA from Blood to Perform Next-Generation Sequencing 10 mL of blood was collected from each of 184 normal subjects and 580 cancer patients, and stored in an EDTA tube. Within 2 hours after blood collection, only the plasma was primarily centrifuged at 1,200 g and 4° C. for 15 minutes, and then the primarily centrifuged plasma was secondarily centrifuged at 16,000 g and 4° C. for 10 minutes to isolate the plasma supernatant excluding the precipitate. Cell-free DNA was extracted from the isolated plasma using a Tiangenmicro DNA kit (Tiangen), a library preparation process was performed using a TruSeq Nano DNA HT library prep kit (Illumina), and then sequencing was performed in a 100 base paired end mode using a DNBseq G400 instrument (MGI). As a result, about 170 million reads were produced for each sample.

Example 2. Production of GC Plot Based on Nucleic Acid Fragment Distance

Figure 2:
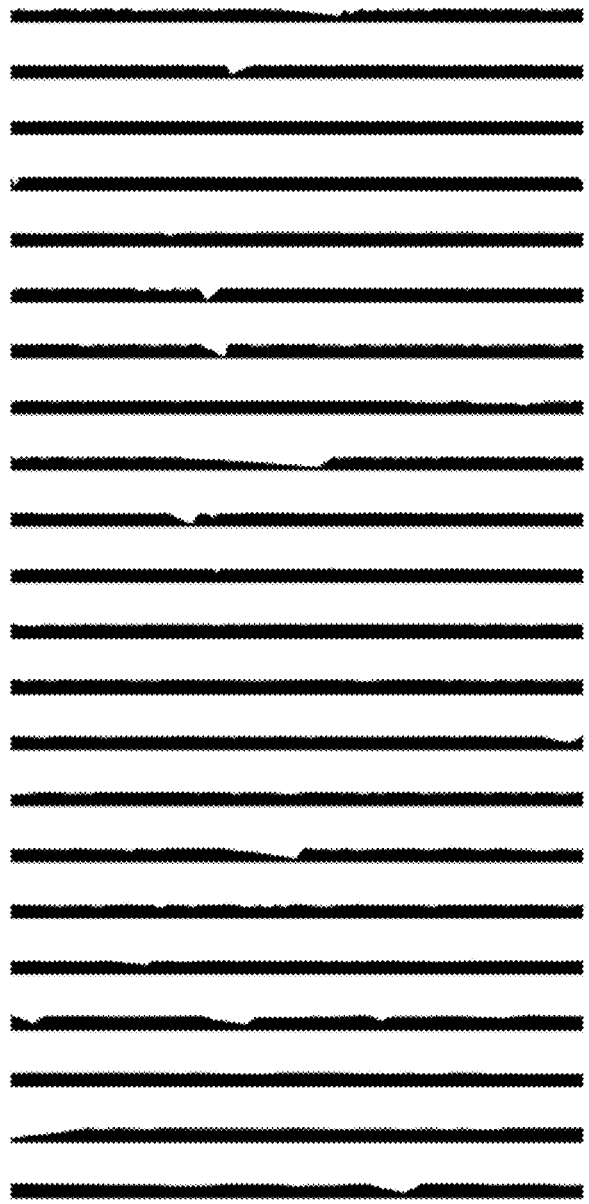
FIG. 2 is an example of a GC plot which is an image obtained by vectorization of NGS data.

A GC plot was formed (vectorized) using the NGS data generated in Example 1 above. The hg19 reference chromosome was divided based on the bin size of 100 k base, and the produced NGS reads were assigned to each bin. Then, the reciprocal of the median of the FD (fragment distance) for each bin was calculated, and an image expressing the position of each bin on the X axis and the reciprocal of the median of the previously calculated FD on the Y axis was created (FIG. 2).

Example 3. CNN Model Construction and Learning Process

Figure 3:
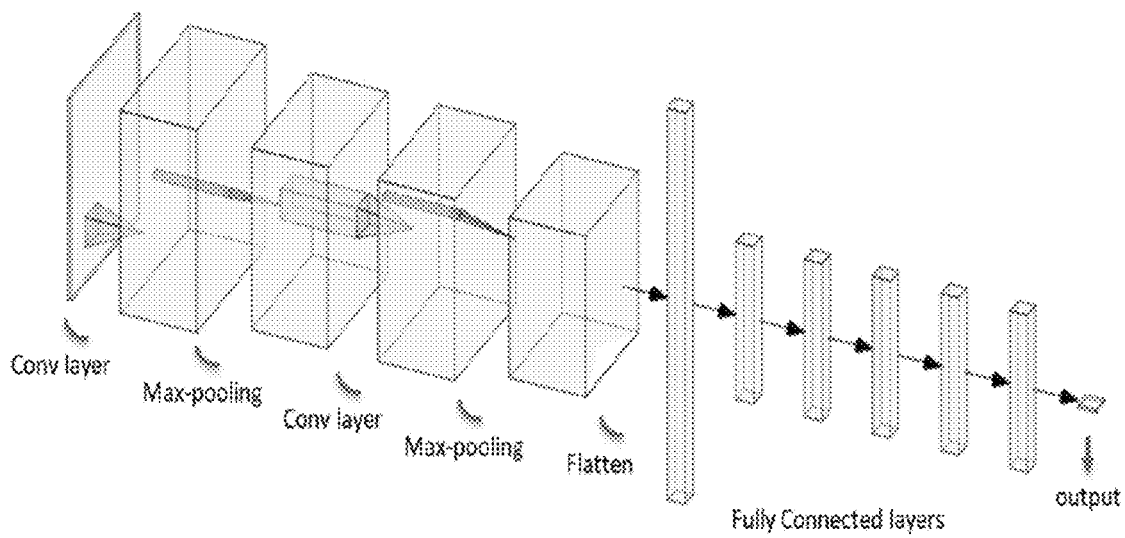
FIG. 3 is a schematic diagram illustrating the configuration of the CNN model according to an embodiment.

The basic configuration of the CNN model is shown in FIG. 3. The activation function used ReLU (rectified linear unit) and each convolution layer used 20 10×10 patches. The pooling mode used herein was max and 2×2 patches were used. Five fully connected layers are used and each layer includes 175 hidden nodes. Finally, the final DPI value was calculated using the sigmoid function value. The hyperparameter values used in the CNN model were obtained through Bayesian optimization and the configuration of the model may vary depending on the data used and optimization of the model.

Example 4. Construction of Cancer Diagnosis Deep-Learning Model Using GC Plot Based on Nucleic Acid Fragment Distance and Performance Testing The performance of the DPI value output from the deep learning model constructed using the GC plot based on the distance between the nucleic acid fragments was tested using the reads obtained in Example 1. All samples were divided into training, validation, and test groups. The models were constructed using the training samples, and then the performance of the models constructed using the training samples was evaluated using the samples of the validation and test groups.

TABLE 1

|  | Normal | Cancer | Total | Baseline accuracy |
|---|---|---|---|---|
| Train | 103 | 316 | 419 | 75.4% |
| Validation | 37 | 113 | 150 | 75.3% |
| Test | 44 | 136 | 180 | 75.6% |
| Total | 184 | 565 | 749 |  |

TABLE 2

|  | Accuracy | AUC |
|---|---|---|
| Train | 100% | 1.0 |
| Validation | 88.7% | 0.95 |
| Test | 90% | 0.938 |

Figure 4:
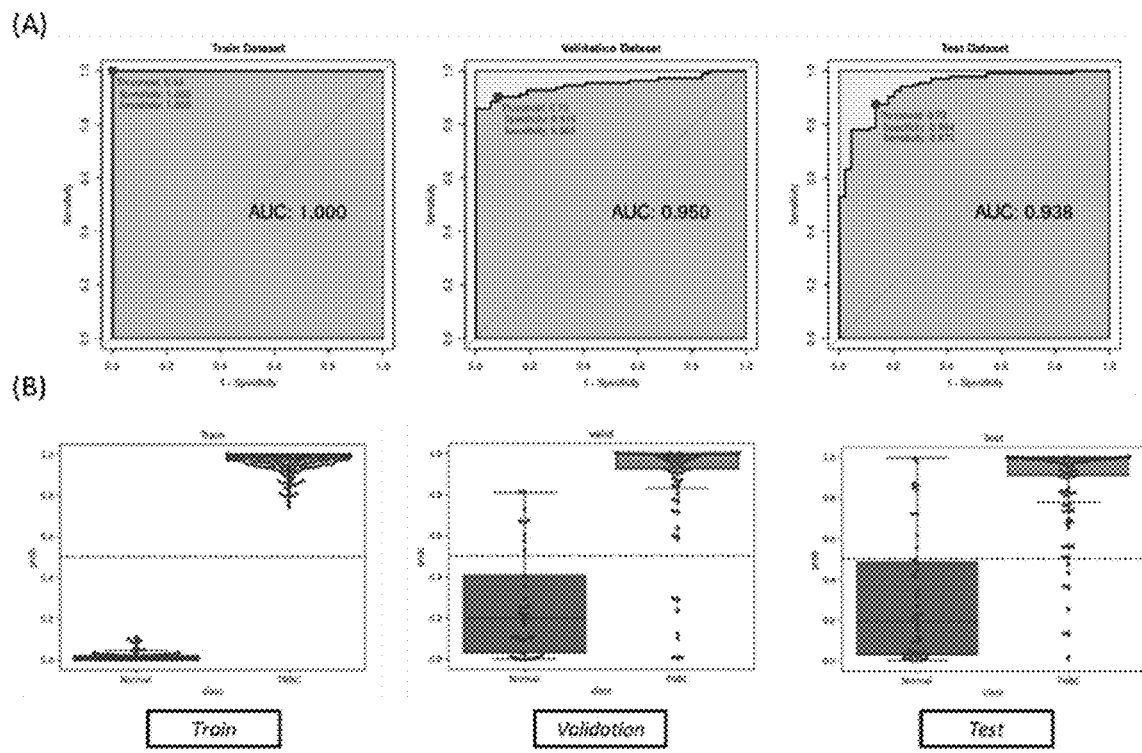
FIG. 4 shows (A) the accuracy of determination as to the presence of cancer for a deep-learning model that had learned the generated GC plot image data and (B) the probability distribution for each data set.

As a result, as can be seen from Table 2 and FIG. 4, accuracy was found to be 100%, 99.7%, and 90% in the training, validation, and test groups, respectively, and the AUC value, which indicates the result of ROC analysis, was found to be 1.00, 0.95, and 0.938 in the training, validation, and test groups, respectively.

FIG. 4 shows (A) the result of analysis using a receiver operating characteristic (ROC) curve to measure accuracy. It is determined that accuracy increases as the area under the curve (AUC) increases. The AUC has a value between 0 and 1, and when the label value is randomly predicted, the expected (baseline) AUC is 0.5, whereas when the label value is correctly predicted, the expected (baseline) AUC is 1.

FIG. 4 shows (B) a boxplot showing the probability value (DPI value) of cancer calculated in the artificial intelligence model of the present invention with respect to normal sample and cancer patient sample groups, wherein the red line represents the DPI cutoff of 0.5.

Example 5. Construction of Cancer Diagnosis Deep-Learning Model Using GC Plot Based on Nucleic Acid Fragment Distance and Performance Testing The performance of the DPI value output from the deep learning model constructed using the GC plot based on the distance between the nucleic acid fragments was tested using the reads obtained in Example 1. All samples were divided into training, validation, and test groups. The models were constructed using the training samples, and then the performance of the models constructed using the training samples was evaluated using the samples of the validation and test groups.

TABLE 3

|  | Normal | Cancer | Total | Baseline accuracy |
|---|---|---|---|---|
| Train | 80 | 325 | 405 | 80.2% |
| Validation | 29 | 116 | 145 | 80% |
| Test | 35 | 139 | 174 | 79.9% |
| Total | 144 | 580 | 724 |  |

TABLE 4

|  | Accuracy | AUC |
|---|---|---|
| Train | 100% | 1.0 |
| Validation | 91% | 0.968 |
| Test | 86.8% | 0.936 |

Figure 5:
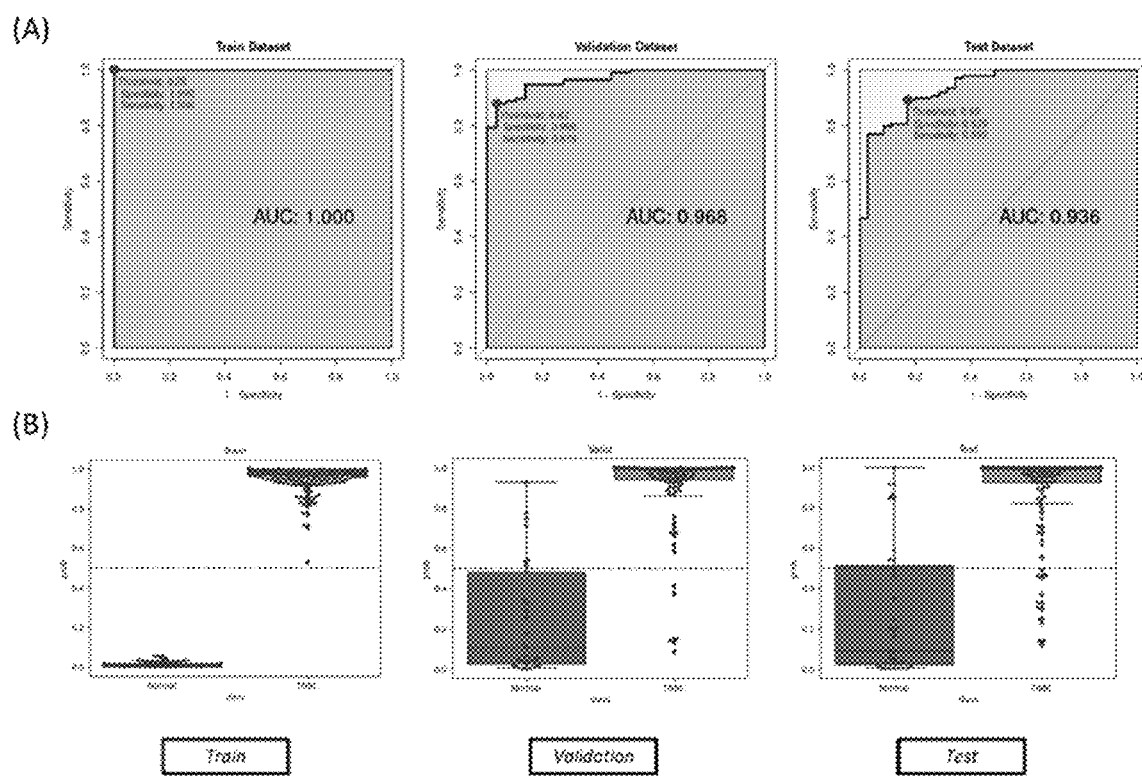
FIG. 5 shows (A) the accuracy of prediction of cancer type for a deep-learning model that had learned the generated GC plot image data and (B) the probability distribution for each data set.

As a result, as can be seen from Table 4 and FIG. 5, accuracy was found to be 100%, 91%, and 86.8% in the training, validation, and test groups, respectively, and the AUC value, which indicates the result of ROC analysis, was found to be 1.0, 0.968, and 0.936 in the training, validation, and test groups, respectively.

FIG. 5 shows (A) the result of analysis using a receiver operating characteristic (ROC) curve to measure accuracy. It is determined that accuracy increases as the area under the curve (AUC) increases. The AUC has a value between 0 and 1, and when the label value is randomly predicted, the expected (baseline) AUC is 0.5, whereas when the label value is correctly predicted, the expected (baseline) AUC is 1.

FIG. 5 shows (B) a boxplot showing the probability value (DPI value) of cancer calculated in the artificial intelligence model of the present invention with respect to normal sample and cancer patient sample groups, wherein the red line represents the DPI cutoff of 0.5.

Although specific configurations of the present invention have been described in detail, those skilled in the art will appreciate that this description is provided to set forth preferred embodiments for illustrative purposes, and should not be construed as limiting the scope of the present invention. Therefore, the substantial scope of the present invention is defined by the accompanying claims and equivalents thereto.

INDUSTRIAL APPLICABILITY

The method of diagnosing cancer and predicting the type of cancer based on artificial intelligence according to the present invention, which includes generating vectorized data and analyzing the same using an AI algorithm, can exhibit similar effects in spite of low read coverage and is thus useful, compared to a method of determining the amount of chromosomes based on the read count, which uses read-related values as standardized values one by one.

The invention claimed is:

1. A method of generating a cancer diagnosis and predicting a type of cancer based on artificial intelligence, the method comprising:
    (a) extracting nucleic acids from a biological sample to obtain sequence information;
    (b) aligning the sequence information consisting of reads with a reference genome database, wherein the sequence information comprises at least 5000 reads;
    (c) generating, by a computer system, vectorized data using nucleic acid fragments derived from the aligned sequence information consisting of reads wherein the vectorized data is a Grand Canyon plot (GC plot) that is generated by
    a process including the following steps:
        c-i) dividing chromosomes into predetermined bins;
        c-ii) calculating a distance between nucleic acid fragments (fragment distance, FD) aligned in each bin:
        c-iii) determining a representative distance between fragments (RepFD) of each bin based on the FD calculated in each bin;
        c-iv) dividing the RepFD calculated in step iii) by a representative total nucleic acid fragment distance to conduct normalization; and
        c-v) creating a GC plot with the order of respective bins on an X-axis and the normalized value calculated in step c-iv) on a Y-axis;
    (d) inputting, by the computer system, the generated vectorized data to a trained artificial intelligence model to generate a resulting output value;
    (e) processing, by the computer system, the resulting output value to generate a cancer diagnosis of whether there is cancer in the biological sample; and
    (f) when the cancer diagnosis is that cancer is present in the biological sample, predicting from said resulting output value a type of cancer that is present in the biological sample.

2. The method according to claim 1, wherein step (a) comprises:
    (a-i) obtaining nucleic acids from blood, semen, vaginal cells, hair, saliva, urine, oral cells, amniotic fluid containing placental cells or fetal cells, tissue cells, or a mixture thereof;
    (a-ii) removing proteins, fats, and other residues from the obtained nucleic acids using a salting-out method, a column chromatography method, or a bead method to obtain purified nucleic acids;
    (a-iii) producing a single-end sequencing or paired-end sequencing library for the purified nucleic acids or nucleic acids randomly fragmented by an enzymatic digestion, pulverization, or hydroshear method;
    (a-iv) reacting the produced library with a next-generation sequencer; and
    (a-v) obtaining sequence information (reads) of the nucleic acids in the next-generation sequencer.

3. The method according to claim 1, wherein the calculating the distribution of the aligned sequence information in each chromosome bin based on the count of nucleic acid fragments is performed using a process including the following steps:
    i) dividing chromosomes into predetermined bins;
    ii) determining the count of nucleic acid fragments aligned in each bin;
    iii) dividing the determined count of nucleic acid fragments in each bin by a total number of nucleic acid fragments in the sample to conduct normalization; and iv) creating a GC plot with an order of respective bins on an X-axis and a normalized value calculated in step iii) on a Y-axis.

4. The method according to claim 1, wherein the RepFD comprises at least one selected from the group consisting of a sum, difference, product, mean, median, quantile, minimum, maximum, variance, standard deviation, median absolute deviation, coefficient of variance of FD, a reciprocal thereof and a combination thereof.

5. The method according to claim 1, wherein the artificial intelligence model of step (d) is trained to distinguish between vectorized data of normal chromosomes and vectorized data of abnormal chromosomes.

6. The method according to claim 5, wherein the artificial intelligence model is selected from the group consisting of a convolutional neural network (CNN), a deep neural network (DNN), a recurrent neural network (RNN), and an autoencoder.

7. The method according to claim 6, wherein, when the artificial intelligence model is a CNN and learns binary classification, a loss function is represented by Equation 1 below:

Equation 1: Binary classification $$\text{loss}(\text{model}(x), y) = -\frac{1}{n}\left[\sum_{i=1}^{n}(y_i \log(\text{model}(x_i)) + (1-y_i)\log(1-\text{model}(x_i)))\right]$$

Model $(x_i)$=Artificial intelligence model output in response to $i^{th}$ input,
y=Actual label value, and
n=Number of input data.

8. The method according to claim 1, wherein the resulting output value through analysis of input vectorized data by the artificial intelligence model in step (d) is a deep probability index (DPI).

9. The method according to claim 1, wherein the processing by the computer system of the resulting output value to generate a cancer diagnosis of whether there is cancer in the biological sample comprises comparing the resulting output value with a cut-off value of 0.5, and when the resulting output value is 0.5 or more, the cancer diagnosis is generated that cancer is present in the biological sample.

10. The method according to claim 1, wherein said predicting a type of cancer in step (e) comprises determining the cancer type showing the highest value among output result values as the cancer of the sample.

11. A non-transitory computer-readable storage medium comprising instructions stored and structurally configured to store data and to accomplish the following steps, for diagnosing cancer and predicting a type of cancer:

(a) extracting nucleic acids from a biological sample to obtain sequence information;
(b) aligning the obtained sequence information consisting of reads (reads) with a reference genome database, wherein the sequence information comprises at least 5000 reads;
(c) generating, by a computer system, vectorized data using nucleic acid fragments derived from the aligned sequence information consisting of reads, wherein the vectorized data is a Grand Canyon plot (GC plot) that is generated by
a process including the following steps:
c-i) dividing chromosomes into predetermined bins;
c-ii) calculating a distance between nucleic acid fragments (fragment distance, FD) aligned in each bin;
c-iii) determining a representative distance between fragments (RepFD) of each bin based on the FD calculated in each bin;
c-iv) dividing the RepFD calculated in step iii) by a representative total nucleic acid fragment distance to conduct normalization; and
c-v) creating a GC plot with the order of respective bins on an X-axis and the normalized value calculated in step c-iv) on a Y-axis;
(d) inputting the generated vectorized data to a trained artificial intelligence model, analyzing a resulting output value, and comparing the resulting output value with a cut-off value to determine whether or not there is cancer; and
(e) analyzing the output result and thereby predicting the type of cancer.

12. The method according to claim 6, wherein, when the artificial intelligence model is the CNN and learns multi-class classification, the loss function is represented by Equation 2 below:

Equation 2: Multi-class classification $$\text{loss}(\text{model}(x), y) = -\frac{1}{n}\sum_{i=1}^{n}\left(\sum_{j=1}^{c}(y_{ij}\log(\text{model}(x_i))_j\right)$$

Model $(x_i)_j$=$j^{th}$ artificial intelligence model output in response to $i^{th}$ input,
y=Actual label value,
n=Number of input data, and
c=Number of classes.

* * * * *

UNITED STATES PATENT AND TRADEMARK OFFICE
CERTIFICATE OF CORRECTION

PATENT NO. : 12,163,194 B2
APPLICATION NO. : 18/003455
DATED : December 10, 2024
INVENTOR(S) : Chang-Seok Ki et al.

Page 1 of 1

It is certified that error appears in the above-identified patent and that said Letters Patent is hereby corrected as shown below:

In the Specification

Column 7, Line 35, "029" should be -- Φ29 --.

In the Claims

Column 28, Lines 5-6, "consisting of reads (reads)" should be -- consisting of reads --.

Signed and Sealed this
Fifteenth Day of July, 2025

Coke Morgan Stewart
*Acting Director of the United States Patent and Trademark Office*